(12) United States Patent  
Israelsson

(10) Patent No.: US 9,944,132 B2  
(45) Date of Patent: Apr. 17, 2018

(54) METHOD FOR ESTIMATING A RELATIVE TIRE FRICTION PERFORMANCE

(71) Applicant: VOLVO CAR CORPORATION, Gothenburg (SE)

(72) Inventor: Erik Israelsson, Gothenburg (SE)

(73) Assignee: Volvo Car Corporation, Gothenburg (SE)

(*) Notice: Subject to any disclaimer, the term of this patent is extended or adjusted under 35 U.S.C. 154(b) by 745 days.

(21) Appl. No.: 14/533,455

(22) Filed: Nov. 5, 2014

(65) Prior Publication Data

US 2015/0135800 A1    May 21, 2015

(30) Foreign Application Priority Data

Nov. 21, 2013  (EP) ..................................... 13193756

(51) Int. Cl.
   *G06F 19/00*  (2011.01)
   *B60C 11/24*  (2006.01)
   (Continued)

(52) U.S. Cl.
   CPC ........... *B60C 11/246* (2013.01); *G01M 17/02* (2013.01); *G01N 19/02* (2013.01); *G08G 1/0112* (2013.01);
   (Continued)

(58) Field of Classification Search
   CPC .................................................... B60C 11/246
   See application file for complete search history.

(56) References Cited

U.S. PATENT DOCUMENTS

2010/0245123 A1* 9/2010 Prasad .................... B60T 8/175
340/870.41

FOREIGN PATENT DOCUMENTS

CN       102984241         3/2013
WO     2005113261 A1    12/2005
(Continued)

OTHER PUBLICATIONS

Chinese Office Action for Chinese Application No. CN 201410641306.5, English Translation attached to original, dated May 25, 2016, All together 20 Pages.
(Continued)

*Primary Examiner* — Phuong Huynh
(74) *Attorney, Agent, or Firm* — Brooks Kushman P.C.

(57) ABSTRACT

A method performed by a network node for estimating a relative tire friction performance of a number of vehicles is disclosed. The network node and a communication unit may be located in each vehicle and may be part of a communications network. The method may include receiving continuously tire-to-road friction values and corresponding VSPs (Vehicle State Parameters) from each communication unit. Each VSP may include the geographical location and time at which tire-to-road friction value is measured. The method may further include determining that a tire-to-road friction value of a first vehicle is comparative to the tire-to-road friction value of a second vehicle. The method may also include comparing the tire-to-road friction value of the first vehicle to the tire-to-road friction value of the second vehicle, and determining a ranking of the relative tire friction performance of the first vehicle in relation to the second vehicle based on the comparison.

15 Claims, 3 Drawing Sheets

(51) Int. Cl.
　　　*G01M 17/02*　　　(2006.01)
　　　*G01N 19/02*　　　(2006.01)
　　　*G08G 1/01*　　　(2006.01)
　　　*G08G 1/0967*　　(2006.01)
　　　*G06F 11/30*　　　(2006.01)
　　　*G01C 21/36*　　　(2006.01)

(52) U.S. Cl.
　　　CPC ..... *G08G 1/0129* (2013.01); *G08G 1/096716* (2013.01); *G08G 1/096741* (2013.01); *G08G 1/096758* (2013.01); *G08G 1/096775* (2013.01); *G01C 21/3697* (2013.01)

(56) References Cited

FOREIGN PATENT DOCUMENTS

| | | | |
|---|---|---|---|
| WO | WO 2005113261 | * | 12/2005 |
| WO | 2012158888 A2 | | 11/2012 |

OTHER PUBLICATIONS

Extended European Search Report Dated Mar. 25, 2014, Application No. 13193756.7-1756, Applicant Volvo Car Corporation, 8 Pages.

\* cited by examiner

METHOD FOR ESTIMATING A RELATIVE TIRE FRICTION PERFORMANCE

CROSS-REFERENCE TO RELATED APPLICATIONS

This application claims foreign priority benefits under 35 U.S.C. § 119(a)-(d) to European patent application number EP 13193756.7 filed on Nov. 21, 2013, the disclosure of which is incorporated herein by reference in its entirety.

TECHNICAL FIELD

The present disclosure relates to a method performed by a network node for estimating a relative tire friction performance of a number of vehicles, wherein said network node and at least one communication unit being located in each vehicle are comprised in a communications network. The disclosure also relates to a network node and a communication unit.

BACKGROUND

Vehicle manufacturers, tire manufacturers and road authorities are striving to reduce low road friction at winter times. The actual road friction is the result not only of the present road conditions but is also affected by the quality of the tires on the vehicle. Inadequate tire friction performance is a serious contributor to insufficient road friction, especially at winter times. No matter how high quality a set of new tires has when a new vehicle is delivered to the first customer, tires will eventually be worn down as mileage is added and tire friction performance may gradually be degraded.

Another potential problem is that a vehicle, that is originally equipped with tires with high road friction quality, selected by the vehicle manufacturer as a part of the vehicle design process, might later be equipped with tires of lower quality and with lower friction performance. In such cases, despite the set of tires being brand new, tire friction performance may still be inferior as compared to high quality tires—in this case, new tires with low friction performance could potentially be deceptive to the driver that is likely to assume that a new set of tires should imply good friction performance.

Since tires will typically be replaced a number of times during the life length of a vehicle, it is not unlikely that some drivers may be unaware of how the set of tires that is mounted on their car actually performs (compared to the unused high performing tires that was originally mounted on the car).

Empirical tests of winter tires have shown that the road friction quality can be very different between tires of different brands; there is indeed a difference in tire quality with respect to road friction performance.

The problem also extends to the usage of "all-weather", "all-season" or "all-year-round" tires in areas with changing weather seasons (e.g., both summer and winter seasons), where the same set of tire often does not have the capacity to deliver sufficient friction performance though the changing weather conditions throughout the whole year. The marketing of "all-year-round" tires may mislead drivers to an incorrect perception that the tires on their vehicle have sufficient friction performance in both summer and winter conditions, since the drivers might be unaware of the relatively low friction performance of their tires as compared to other high performing season tires (i.e., summer and winter tires) that are designed for optimal performance on the more specific road conditions that are typical for either winter or summer.

In view of the above, there is a need to estimate the quality of the tires of a vehicle, so as to determine the tires ability to provide sufficient road friction.

WO2012/158888 describes a method for performing a field survey including a large amount of data relating to tires. The tire data collected includes tire pattern, tire brand and serial number, tire position in the vehicle, tire option code, air pressure, mounting date, etc. Moreover, tire wear information such as depth, width and length of irregular thread wear is collected. The information collected may be used for estimating e.g., how many more miles a tire may safely drive. The tire data may be collected e.g., during a planned service of the vehicle.

Although the method described in WO2012/158888 might be useful for estimating certain qualities with tires which may have an impact on their ability to provide sufficient road friction, it lacks a possibility of evaluating how the tires perform in real-life conditions.

Accordingly, there is still a need to provide an improved method for estimating the quality of the tires of a vehicle.

SUMMARY

It is an object of embodiments herein to improve the estimation of the quality of the tires of the vehicle.

According to a first aspect of embodiments herein, the object is achieved by a method performed by a network node for estimating a relative tire friction performance of a number of vehicles, wherein said network node and at least one communication unit being located in each vehicle are comprised in a communications network, the method comprising receiving (201) continuously tire-to-road friction values (f) and corresponding VSPs (Vehicle State Parameters) (l, t) from each communication unit in the number of vehicles (v) during the driving thereof, each VSP comprising at least the geographical location (l) at which the tire-to-road friction value (f) is measured, and the instant in time (t) when the tire-to-road friction value (f) is measured; the method further comprising: determining (202) that a tire-to-road friction value (f1) of a vehicle (v1) in the number of vehicles (v) is comparative to at least one other tire-to-road friction value (f2) of another vehicle (v2) in the number of vehicles (v), when the corresponding VSP (l2, t2) of said at least one other tire-to-road friction value (f2) deviates less than a predetermined deviation range from the corresponding VSP (l1,t1) of the tire-to-road friction value (f1) of a vehicle (v1); comparing (203) the tire-to-road friction value (f1) of the vehicle (v1) to the at least one other tire-to-road friction value (f2) of the another vehicle (v2); and determining (204) a ranking of the relative tire friction performance of the vehicle (v1) in relation to at least the another vehicle (v2) based on said comparison.

According to a second aspect of embodiments herein, the object is achieved by a network node for estimating a relative tire friction performance of vehicles, wherein said network node and at least one communication unit for each of a number of vehicles are comprised in a communications network, the network node comprising processing circuitry configured to receive continuously tire-to-road friction values and corresponding VSPs (Vehicle State Parameters) from each communication unit in the number of vehicles during the driving thereof, each VSP comprising at least the geographical location at which the tire-to-road friction value is measured, and the instant in time when the tire-to-road friction value is measured; wherein the processing circuitry is further configured to determine that a tire-to-road friction value of a vehicle in the number of vehicles is comparative to at least one other tire-to-road friction value of another vehicle in the number of vehicles, when the corresponding VSP of said at least one other tire-to-road friction value deviates less than a predetermined deviation range from the corresponding VSP of the tire-to-road friction value of a vehicle; to compare the tire-to-road friction value of the vehicle to the at least one other tire-to-road friction value of the another vehicle; and to determine a ranking of the relative tire friction performance of the vehicle in relation to at least the another vehicle based on said comparison.

According to third aspects of embodiments herein, this object is achieved by a communication unit located in a vehicle comprising equipment for continuously rendering available a tire-to-road friction value (f) and a corresponding VSP (Vehicle State Parameter) (l, t) during the driving of the vehicle, each VSP comprising at least the geographical location (l) at which the tire-to-road friction value (f) is measured, and the instant in time (t) when the tire-to-road friction value (f) is measured; equipment for receiving a result indicating a relative tire friction performance of the vehicle, and equipment for displaying said result to a driver of the vehicle.

A tire-to-road friction value measured for a vehicle, will depend on a number of factors, and in particular on the tire quality and the road condition. In accordance with what is proposed herein, tire-to-road friction values from driving vehicles are treated together with corresponding VSPs, which VSPs include at least the geographical location (l) at which the tire-to-road friction value (f) is measured, and the instant in time (t) when the tire-to-road friction value (f) is measured.

Hence, in accordance with the proposed method, a number of tire-to-road friction values will continuously be retrieved from a number of vehicles when driving. Out of the number of tire-to-road friction values retrieved, such tire-to-road friction values which are retrieved from vehicles which are geospatially close to each other, and at instants in time which are temporally close to one another, are deemed to be comparable. In other words, vehicles that are on approximately the same location at about the same time, are believed to experience similar road conditions. Accordingly, the difference in tire-to-road friction values measured by such vehicles may be attributed primarily to the difference in tire quality between the vehicles. Hence, a tire-to-road friction value of a vehicle is comparative to other tire-to-road friction values of other vehicles, when their corresponding VSPs deviates less than a predetermined deviation range.

The comparative tire-to-road friction values are used to create a ranking of the vehicles based on the vehicles' tire friction performance.

In the number of VPS retrieved from the number of vehicles, several sets of comparative VPS may be defined, and used to create said ranking of the vehicles. It is believed that the ranking quality may be improved with the size of the number of vehicles evaluated, and the extension of the time period during which the method is performed for the number of vehicles.

Hence, estimation of the quality of the tires of a vehicle is improved.

BRIEF DESCRIPTION OF THE DRAWINGS

Features and advantages of the embodiments will become readily apparent to those skilled in the art by the following detailed description of exemplary embodiments thereof with reference to the accompanying drawings.

DETAILED DESCRIPTION

Figure 1:
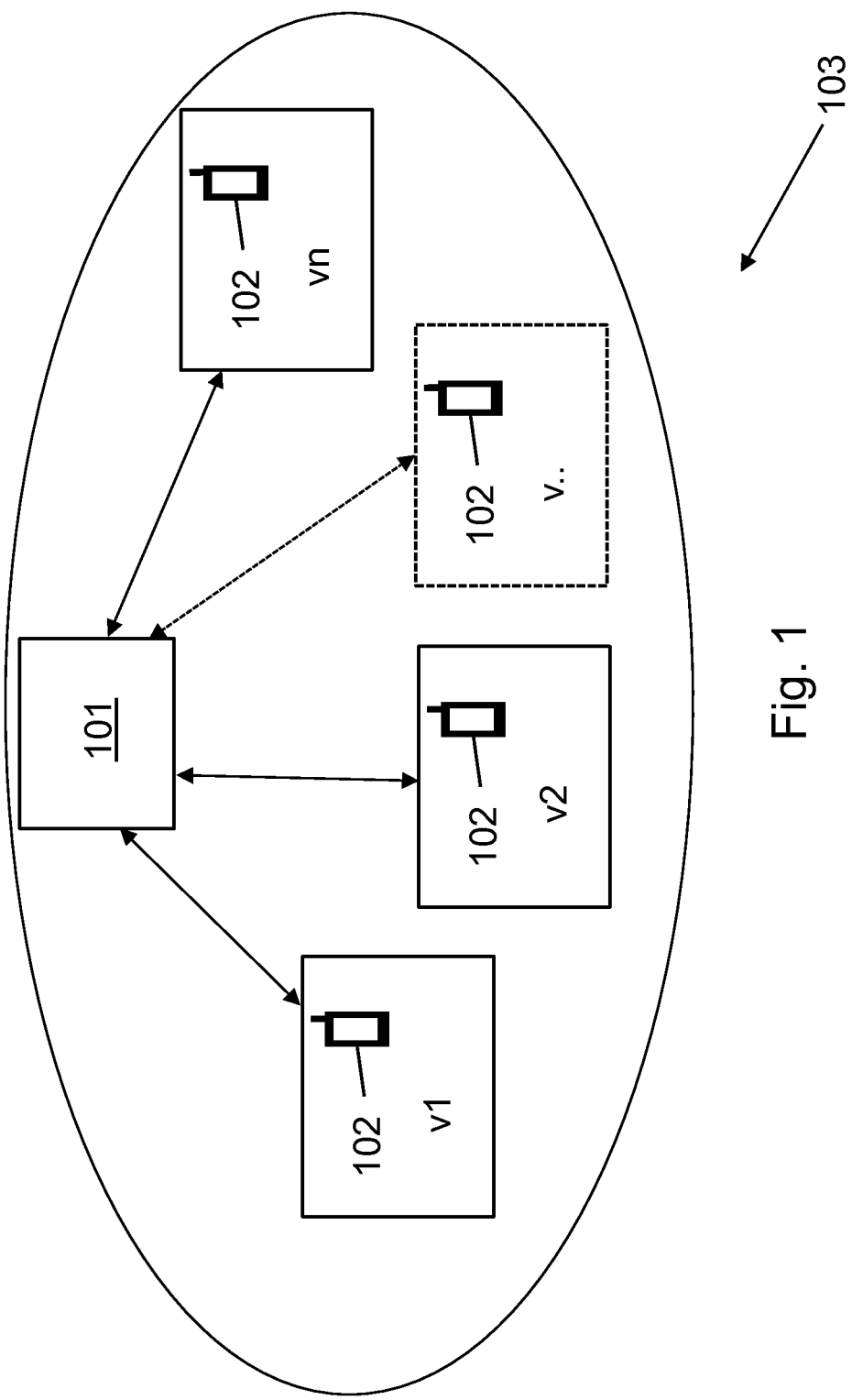
FIG. 1 is a schematic illustration of a wireless telecommunications network comprising a network node and communication units located in a number of vehicles.

As required, detailed embodiments are disclosed herein. However, it is to be understood that the disclosed embodiments are merely exemplary and that various and alternative forms may be employed. The figures are not necessarily to scale. Some features may be exaggerated or minimized to show details of particular components. Therefore, specific structural and functional details disclosed herein are not to be interpreted as limiting, but merely as a representative basis for teaching one skilled in the art.

The figures are schematic and simplified for clarity, and show sufficient details for the understanding of the embodiments presented herein, while other details have been left out. Throughout, the same reference numerals are used for identical or corresponding parts or steps.

FIG. 1 depicts an example of a communications network 103 in which the embodiments described herein may be implemented. The communications network 103 comprises a network node 101, and a number of communication units 102, each communication unit being located in one out of a number of vehicles (v).

Each communication unit 102 may be configured to wirelessly communicate with the network node 101 via any suitable communications network, such as, for example, a wireless telecommunications network and/or data communications network. For handling the communication between the network node 101 and the communication units 102, the wireless telecommunications network may utilize any suitable radio communication technology, for example, the Radio Access Technology, RAT, utilized may comprise any one or several of GSM, WCDMA, LTE, WiFi or other wireless technologies.

Method

Figure 2:
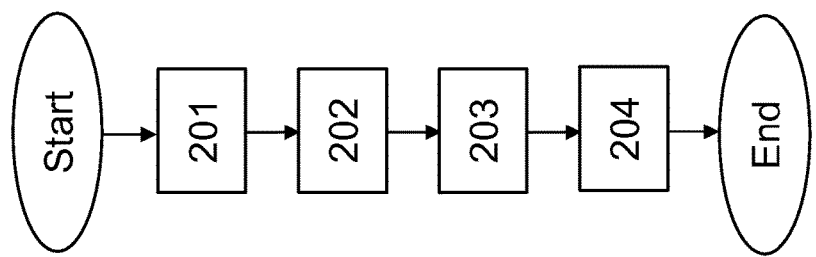
FIG. 2 is a flowchart depicting embodiments of a method in a network node.

Example of embodiments of a method performed by a network node 101 for estimating a relative tire friction performance of a number of vehicles vn, will now be described with reference to a flowchart depicted in FIG. 2. Here, the network node 101 and at least one communication unit 102 being located in each vehicle vn are comprised in a communications network, such as, e.g. the communications network 103 in FIG. 1. FIG. 2 is an illustrated example of exemplary actions or operations which may be taken by the network node 101.

The method may comprise the following actions.

Action 201

In this action, the network node 101 receives continuously tire-to-road friction values (f) and corresponding VSPs (Vehicle State Parameters) (l, t) from each communication unit in the number of vehicles (v) during the driving thereof, each VSP comprising at least the geographical location (l) at which the tire-to-road friction value (f) is measured, and the instant in time (t) when the tire-to-road friction value (f) is measured.

By "receiving continuously" is meant that the network node receives a number of values and parameters over time. The frequency at which individual values and corresponding parameters are received may vary.

For example, the generation of a tire-to-road friction value for a vehicle may be initiated by an event occurring during drive of a vehicle, such as when a stability function in the vehicle is active. This would typically correspond to events such as acceleration or retardation of the vehicle, or when the vehicle is travelling in curvatures. Accordingly, tire-to-road friction values for a vehicle may be generated at such discreet and randomly occurring events. In this case, the tire-to-road friction values and corresponding VSPs for the vehicle may be transmitted to the network node via the communication unit at randomly occurring (non-continuous) points in time. Nevertheless, it is considered herein that the network node will "continuously receive" data.

In other embodiments, the generation of tire-to-road friction values may be performed e.g., at a pre-defined frequency. This will also result in the network node "continuously receiving" data, as defined herein.

By "receiving" is meant both active retrieval of data initiated from the network node, and passive receiving of data to the network node. The network node might actively initiate retrieval of values and parameters. However, the network node may also passively receive values which are emitted from the communication units.

A tire-to-road friction value is a value indicative of the friction between the road and the tire during driving. For enabling the comparison of the tire-to-road friction values retrieved from the vehicles, they should advantageously be of the same type; that is, be generated by comparative measurement methods and/or calculated using similar algorithms. One example of a definition of a tire-to-road friction value is the maximum horizontal force normalized by the vertical force that can be produced between each tire of the vehicle and the road.

Numerous methods for measuring a tire-to-road friction value are known in the art and may be used for generating values for use with the present disclosure.

The geographical location in the VSP may be determined using e.g., GPS system. This may include comparing said geographical coordinates to a map database, and determining additional geographical information using said map database, for example on which road the vehicle is travelling. Then, the method may further comprise determining that a tire-to-road friction value (f1) of a vehicle (v1) is comparative to at least one other tire-to-road friction value (f2) of another vehicle (v2) in the number of vehicles, when the corresponding additional geographical information indicates similar road conditions for the vehicles (v1, v2).

Accordingly, it may for example be possible to deem VSPs from two vehicles travelling on the same main road to be comparable, whilst a VSP from a vehicle being close to the two other vehicles, but driving on a smaller road running in parallel with the main road, will not be deemed comparable with the other two.

The instant in time (t) in the VSP may also be determined using a GPS system.

Hence, a GPS system may provide both the geographical location (l) and the instant in time (t) when the tire-to-road friction value (f) is measured.

It will be understood that the method may be performed considering tire-to-road friction values from at least one tire of each vehicle, as well as on all tires of each vehicle.

Action 202

In this action, the network node 101 determines that a tire-to-road friction value (f1) of a vehicle (v1) in the number of vehicles (v) is comparative to at least one other tire-to-road friction value (f2) of another vehicle (v2) in the number of vehicles (v), when the corresponding VSP (l2, t2) of said at least one other tire-to-road friction value (f2) deviates less than a predetermined deviation range from the corresponding VSP (l1,t1) of the tire-to-road friction value (f1) of a vehicle (v1).

In accordance with the proposed method, tire-to-road friction values from driving vehicles are treated together with corresponding VSPs, which VSPs include at least a the geographical location (l) at which the tire-to-road friction value (f) is measured, and the instant in time (t) when the tire-to-road friction value (f) is measured.

A tire-to-road friction value measured for a vehicle, will depend on a number of factors, and in particular on the tire quality and the road condition.

In accordance with the method as proposed herein, tire-to-road friction values which are retrieved from vehicles which are geospatially close to each other, and at instants in time which are temporally close to one another, are deemed to be comparable. In other words, vehicles that are on approximately the same location at about the same time, are believed to experience similar road conditions. Accordingly, the difference in tire-to-road friction values measured by such vehicles, may be attributed primarily to the difference in tire quality between the vehicles. Hence, a tire-to-road friction value is comparative to other tire-to-road friction values of other vehicles, when their corresponding VSPs deviates less than a predetermined deviation range.

In accordance with embodiments, the corresponding VSP (l2, t2) of said at least one other tire-to-road friction value (f2) deviates less than a predetermined deviation range from the corresponding VSP (l1,t1) of the tire-to-road friction value (f1) of a vehicle (v1) only if the difference between the location (l1) and/or instant (t1) of the corresponding VSP (l1, t1) of the tire-to-road friction value (f1) of a vehicle (v1) and the location (l2) and/or instant (t1) of the corresponding VSP (l2, t2) of the another tire-to-road friction value (f2) is less than a present predetermined location deviation L and/or a present predetermined time deviation T.

The predetermined location deviation and the predetermined time deviation may be fixed values, but the predetermined location deviation and the time deviation may be dynamic values being set depending on the circumstances during which the road conditions may be deemed comparable.

In accordance with embodiments, the method comprises receiving information regarding the environmental conditions surrounding the vehicle (v1) and setting said location deviation L and/or time deviation T depending on the information regarding the environmental conditions surrounding the vehicle (v1).

The location deviation and/or the time deviation may be continuously updated and reset depending on the environmental conditions. Also, rather than considering each vehicle one by one, the time deviation and location deviation may be simultaneously set for a group of vehicles, or for e.g., a geographical area.

Advantageously, the environmental conditions comprise at least one of: weather conditions, ambient light conditions, and road conditions.

Information regarding the environmental conditions around a vehicle may be gathered by conventional methods which may include sensors attached to the vehicle.

Apart from the road conditions and the tire friction performance, the tire-to-road friction value may be affected by other features, some of which may be definable in the VSP and thereby removed from affecting the ranking of the vehicle.

One such feature is the vehicle configuration.

According to embodiments, each VSP further comprises a parameter including information regarding the vehicle configuration (c1) of the vehicle.

With "vehicle configuration" is meant herein physical features of the vehicle which may be defined and which may affect the tire-to-road friction value.

Advantageously, the corresponding VSP (l2, t2,c2) of said at least one other tire-to-road friction value (f2) deviates less than a predetermined deviation range from the corresponding VSP (l1, t1, m1) of the tire-to-road friction value (f1) of a vehicle (v1) only if also said vehicle configurations (c1, c2) are deemed comparable.

The vehicle configuration may include at least one out of the vehicle's weight and its powertrain arrangement. Both of these features are believed to influence the tire-to-road friction values.

Hence, the method may further comprise that the determination whether the vehicle configurations are comparable includes a comparison of at least one out of the vehicle's weight and powertrain arrangement.

For performing comparisons related to the vehicle configurations, it is envisaged that vehicles may be divided into groups having similar properties, and the VSPs of the vehicles be prepared so as to include an indication of in which group the vehicle would belong.

An information regarding the vehicle configuration may be static configuration information or dynamic configuration information. Static configuration information, such as powertrain arrangement and vehicle model, may, if desired, be received only once by the network node, and then repeatedly be used for the relevant vehicle. Dynamic configuration information such as vehicle weight may be continuously received with the VSP.

In accordance with the above, a method is proposed wherein a ranking of the tire friction performance of vehicles may be achieved, such as by separating the influence from the tire friction from the influence from road conditions and the vehicle configuration on the tire-to-road friction values.

Action 203

In this action, the first network node 101 compares the tire-to-road friction value (f1) of the vehicle (v1) to the at least one other tire-to-road friction value (f2) of the another vehicle (v2).

Action 204

In this action, the first network node 101 determines a ranking of the relative tire friction performance of the vehicle (v1) in relation to at least the another vehicle (v2) based on said comparison.

The comparative tire-to-road friction values are used to create a ranking of the vehicles based on the vehicles' tire friction performance.

Said ranking may be continuously updated over a period of time. As friction values between comparative vehicles are received over a period of time and for a number of vehicles, rankings between comparative vehicles will be added to the overall ranking of the vehicles, meaning that the accuracy of the overall ranking will be improved as the number of treated values is increased. It is envisaged that the method may be run for a rather long period of time, e.g., more than a month or several months.

In accordance with embodiments, the method may further comprise rendering information regarding the ranking available to the communication unit located in the vehicle. Advantageously, the information may further be displayed to the driver of the vehicle. Hence, the driver may receive information of the relative tire friction performance of the tires of the vehicle.

If the relative tire friction performance is poor, this may be due to wear of the tires, improper tires for the vehicle or for the season, and the driver may consider changing to better adapted tires.

In accordance with embodiments, the method may comprise: retrieving said ranking, performing a statistical evaluation of the ranking, and determining preselected relative tire friction performance levels based on said evaluation, sorting the relative tire friction performance of the number of vehicles (vn) into groups based on the relative tire friction performance levels, and rendering information about the group of the vehicle (v1) available to the communication unit located in the vehicle (v1).

Suitable levels and groups may correspond to statistical features e.g. defining an "average friction performance", a "first quartile performance," etc.

In accordance with embodiments, the method may further comprise retrieving the number of comparative road friction values available in said data system, determining whether said number is sufficient for performing a statistically valid analysis, and generating a present validity status of the ranking based on said determination.

It is understood that the statistical validity of the ranking will be better the more values used as input, and the longer period of time that the method is run and the ranking is updated. In accordance with the above, the method will determine when the ranking may be deemed valid, as a whole or for a selected vehicle.

In accordance with embodiments, the method may further comprise determining that the tire-to-road friction value (f1) of the vehicle (v1) deviates more than a predetermined variation range from a previous tire-to-road friction value (f1) of the vehicle (v1); determining that the variation is indicative of a change in conditions for that vehicle (v1); and deeming a VSP from the vehicle (v1) to be comparable a VSP from another vehicle (v2) only if the instants in time (t1, t2) and/or the geographical locations (l1,l2) of both VSPs are both before or after said change.

If a tire-to-road friction value f1 of a vehicle v1 deviates more than a predetermined deviation range from a previous tire-to-road friction value f1 of the same vehicle v1, it considered that something unusual has occurred.

A variation analysis may be performed to determine the art of the variation.

It may be determined that the deviating road-to-friction value f1 was due to an error or to an isolated event, resulting in the deviating road-to-friction value f1 to be disregarded, and deemed incomparable to any other values.

However, the variation analysis may determine that the deviating road-to-friction value f1 is indicative of a change in conditions experienced by the vehicle. Such a change in conditions could for example be a sudden snowfall, a rising or falling temperature, etc. If the deviating road-to-friction value is indicative of a change in conditions, then only VSPs taken before or after said change in conditions are deemed comparable.

In the above, it has been described how an improved ranking between vehicles may be achieved. Now, having the ranking between vehicles, it will be possible also to gather information regarding the road conditions using the tire-to-road friction values, and removing the influence from the tire friction performance.

Accordingly, it is proposed that the network node further comprises a map database including a geographical road condition status for the roads in the map database, and the method further comprises weighing at least one tire-to-road friction value (f1) of a vehicle (v1) using said ranking so as to achieve at least one normalized road friction value (nf1); and generating an updated geographical road condition status for the geographic map database using the at least one normalized road friction value (nf1).

In accordance with the above, the ranking is used to create normalized road friction values: i.e., road friction values from which the relative influence of the tire friction performance is removed. Accordingly, the normalized road friction values from different vehicles are comparable and may be used to update a map database including a road condition status.

Accordingly, the method proposed in the above may be used to create a map including updated road condition status for the roads in the map. The information regarding the road condition status may be used and spread to inform drivers, not only of the vehicles considered by the method, but any drivers of the present road conditions.

In accordance with embodiments, the method may further comprise rendering information about the geographical road condition status in the geographic map database available to the communication units of the vehicles.

For examples, a warning may be issued that a vehicle is driving on a road where poor road conditions prevails, motivating the driver to drive carefully, e.g., to lower the driving speed.

Network Node

Figure 3:
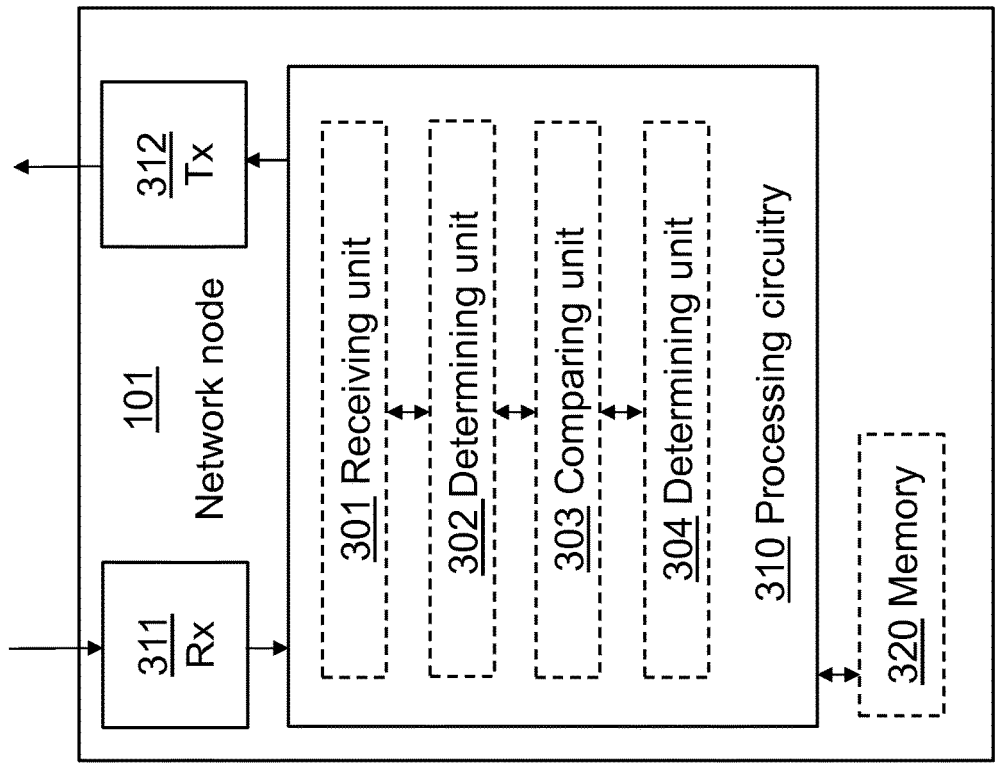
FIG. 3 is a block diagram depicting embodiments of a network node.
Figure 4:
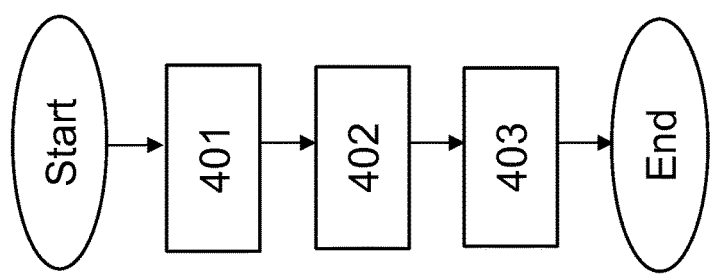
FIG. 4 is a flowchart depicting embodiments of a method in a communication unit.

To perform the method actions in the first network node 101 for estimating a relative tire friction performance of vehicles, the first network node 101 may comprise the following arrangement depicted in FIGS. 3 and 4.

FIG. 3 shows a schematic block diagram of embodiments of the first network node 101. The first network node is configured to be comprised in a communications network with at least one communication unit being located in each out of a number of vehicles.

The first network node 101 may comprise a processing circuitry 310, which may also be referred to as a processor or a processing unit. The processing circuitry 310 is configured to receive 301 continuously tire-to-road friction values (f) and corresponding VSPs (Vehicle State Parameters) (l, t) from each communication unit in the number of vehicles (v) during the driving thereof, each VSP comprising at least the geographical location (l) at which the tire-to-road friction value (f) is measured, and the instant in time (t) when the tire-to-road friction value (f) is measured; wherein the processing circuitry is further configured to determine 302 that a tire-to-road friction value (f1) of a vehicle (v1) in the number of vehicles (v) is comparative to at least one other tire-to-road friction value (f2) of another vehicle (v2) in the number of vehicles (v), when the corresponding VSP (l2, t2) of said at least one other tire-to-road friction value (f2) deviates less than a predetermined deviation range from the corresponding VSP (l1, t1) of the tire-to-road friction value (f1) of a vehicle (v1); to compare 303 the tire-to-road friction value (f1) of the vehicle (v1) to the at least one other tire-to-road friction value (f2) of the another vehicle (v2); and to determine 304 a ranking of the relative tire friction performance of the vehicle (v1) in relation to at least the another vehicle (v2) based on said comparison.

Moreover, the processing circuitry may be configured to execute any of the actions as described in the above, in relation to the method proposed herein, alone or in combination.

The first network node may comprise a receiving unit 301 which may also be referred to as a receiving device or circuitry. The receiving unit 301 is configured to receive continuously tire-to-road friction values (f) and corresponding VSP's (l, t) from each communication unit in the number of vehicles (v) during the driving thereof.

The first network node may comprise a determining unit 302, which may also be referred to as a determining device or circuitry. The determining unit 302 is configured to determining that a tire-to-road friction value (f1) of a vehicle (v1) in the number of vehicles (v) is comparative to at least one other tire-to-road friction value (f2) of another vehicle (v2) in the number of vehicles (v), when the corresponding VSP (l2, t2) of said at least one other tire-to-road friction value (f2) deviates less than a predetermined deviation range from the corresponding VSP (l1, t1) of the tire-to-road friction value (f1) of a vehicle (v1).

In accordance with embodiments, the determining unit 302 may be configured to determining that the corresponding VSP (l2, t2) of said at least one other tire-to-road friction value (f2) deviates less than a predetermined deviation range from the corresponding VSP (l1, t1) of the tire-to-road friction value (f1) of a vehicle (v1) only if the difference between the location (l1) and/or instant (t1) of the corresponding VSP (l1, t1) of the tire-to-road friction value (f1) of a vehicle (v1) and the location (l2) and/or instant (t1) of the corresponding VSP (l2, t2) of the another tire-to-road friction value (f2) is less than a present predetermined location deviation L and/or a present predetermined time deviation T.

In accordance with embodiments, the receiving unit 301 may be configured to receiving information regarding the environmental conditions surrounding the vehicle (v1) and the determining unit 302 may utilize location deviation L and/or time deviation T being set depending on the information regarding the environmental conditions surrounding the vehicle (v1).

Advantageously, the environmental conditions comprise at least one of: weather conditions, ambient light conditions, and road conditions.

According to embodiments, each VSP further comprises a parameter including information regarding the vehicle configuration (c1) of the vehicle.

With "vehicle configuration" is meant herein physical features of the vehicle which may be defined and which may affect the tire-to-road friction value.

Advantageously, the determining unit 302 may be configured to determining that the corresponding VSP (l2, t2,c2) of said at least one other tire-to-road friction value (f2) deviates less than a predetermined deviation range from the corresponding VSP (l1, t1, m1) of the tire-to-road friction value (f1) of a vehicle (v1) only if also said vehicle configurations (c1, c2) are deemed comparable.

The vehicle configuration may include at least one out of the vehicle's weight and its powertrain arrangement. Both of these features are believed to influence the tire-to-road friction values.

Hence, the determination whether the vehicle configurations are comparable may include a comparison of at least one out of the vehicle's weight and powertrain arrangement.

The first network node may comprise a comparing unit 303, which may also be referred to as a comparing device or circuitry. The comparing unit 303 is configured to compare the tire-to-road friction value (f1) of the vehicle (v1) to the at least one other tire-to-road friction value (f2) of the another vehicle (v2).

The first network node may comprise a second determining unit 304, which may also be referred to as a determining device or circuitry. The determining unit 304 is configured to determine (304) a ranking of the relative tire friction performance of the vehicle (v1) in relation to at least the another vehicle (v2) based on said comparison.

In accordance with embodiments, the second determining unit 304 may moreover be configured for: retrieving said ranking, performing a statistical evaluation of the ranking, and determining preselected relative tire friction performance levels based on said evaluation, sorting the relative tire friction performance of the number of vehicles (vn) into groups based on the relative tire friction performance levels, and rendering information about the group of the vehicle (v1) available to the communication unit located in the vehicle (v1).

Suitable levels and groups may correspond to statistical features e.g., defining an "average friction performance", a "first quartile performance," etc.

In accordance with embodiments, the second determining unit 304 may advantageously be configured for retrieving the number of comparative road friction values available in said data system, determining whether said number is sufficient for performing a statistically valid analysis, and generating a present validity status of the ranking based on said determination.

It is understood that the statistical validity of the ranking will be better the more values used as input, and the longer period of time that the method is run and the ranking is updated. In accordance with the above, the method will determine when the ranking may be deemed valid, as a whole or for a selected vehicle.

In accordance with embodiments, the second determining unit 304 may be configured for determining that the tire-to-road friction value (f1) of the vehicle (v1) deviates more than a predetermined variation range from a previous tire-to-road friction value (f1) of the vehicle (v1); determining that the variation is indicative of a change in conditions for that vehicle (v1); and deeming a VSP from the vehicle (v1) to be comparable a VSP from another vehicle (v2) only if the instants in time (t1, t2) and/or the geographical locations (l1, l2) of both VSPs are both before or after said change.

According to embodiments, the network node further comprise map updating unit, utilizing a map database including a geographical road condition status for the roads in the map database, and being configured for weighing at least one tire-to-road friction value (f1) of a vehicle (v1) using said ranking so as to achieve at least one normalized road friction value (nf1); and generating an updated geographical road condition status for the geographic map database using the at least one normalized road friction value (nf1).

The processing circuitry 310 may comprise the receiving unit 301, the determining unit 302, the comparing unit 303 and the determining unit 304.

The processing circuitry 310 may further comprise a receiver or receiving unit 311 and a transmitter or transmitting unit 312 for receiving/transmitting information to/from communication units. The receiving and transmitting unit 311, 312 may alternatively be constituted by a transceiving unit.

In accordance with embodiments, the transmitting unit 312 may be configured for rendering information regarding the ranking available to the communication unit located in the vehicle. Advantageously, the information may further be displayed to the driver of the vehicle. Hence, the driver may receive information of the relative tire friction performance of the tires of the vehicle.

In accordance with embodiments, the transmitting unit may be configured for rendering information about the geographical road condition status in the geographic map database available to the communication units of the vehicles.

The embodiments for estimating relative tire friction performance for a number of vehicles may be implemented through one or more processors, such as the processing circuitry 310 in the first network node 101 depicted in FIG. 3, together with computer program code for performing the functions and actions of the embodiments herein. The program code mentioned above may also be provided as a computer program product, for instance in the form of a data carrier carrying computer program code or code means for performing the embodiments herein when being loaded into the processing circuitry 310 in the first network node 101. The computer program code may e.g., be provided as pure program code in the first network node 101 or on a server and downloaded to the first network node 101.

The first network node 101 may further comprise a memory 320 comprising one or more memory units. The memory 320 may be arranged to be used to store data, such as, e.g., the tire-to-road friction values and corresponding VSPs received from the communication units, to perform the methods herein when being executed in the first network node 101.

Those skilled in the art will also appreciate that the processing circuitry 310 and the memory 320 described above may refer to a combination of analog and digital circuits, and/or one or more processors configured with software and/or firmware, e.g., stored in a memory, that when executed by the one or more processors such as the processing circuitry 310 perform as described above. One or more of these processors, as well as the other digital hardware, may be included in a single application-specific integrated circuit (ASIC), or several processors and various digital hardware may be distributed among several separate components, whether individually packaged or assembled into a system-on-a-chip (SoC).

Communication Unit Method

Example of embodiments of a method performed by a communication unit (102) for displaying a result including estimation of a relative tire friction performance of a number of vehicles (vn), will now be described with reference to a flowchart depicted in FIG. 4. Here, the network node 101 and at least one communication unit 102 being located in each vehicle vn are comprised in a communications network, such as, e.g., the communications network 103 in FIG. 1. FIG. 4 is an illustrated example of exemplary actions or operations which may be taken by the communication unit 102.

The method may comprise the following actions:

Action 401

In this action, the communications unit renders available a tire-to-road friction value (f) and a corresponding VSP (Vehicle State Parameter) (l, t) during the driving of the vehicle, each VSP comprising at least the geographical location (l) at which the tire-to-road friction value (f) is measured, and the instant in time (t) when the tire-to-road friction value (f) is measured.

Action 402

In this action, the communications unit receives a result indicating a relative tire friction performance of the vehicle.

Action 403

In this action, the communications unit displays said result to a driver of the vehicle.

Communication Unit

In accordance with a third aspect, the object of the disclosure is solved by, a communication unit located in a vehicle comprising: processing circuitry 510 configured to continuously render 401 available a tire-to-road friction value (f) and a corresponding VSP (Vehicle State Parameter) (l, t) during the driving of the vehicle, each VSP comprising at least the geographical location (l) at which the tire-to-road friction value (f) is measured, and the instant in time (t) when the tire-to-road friction value (f) is measured, receive 402 a result indicating a relative tire friction performance of the vehicle, and display 403 said result to a driver of the vehicle.

Figure 5:
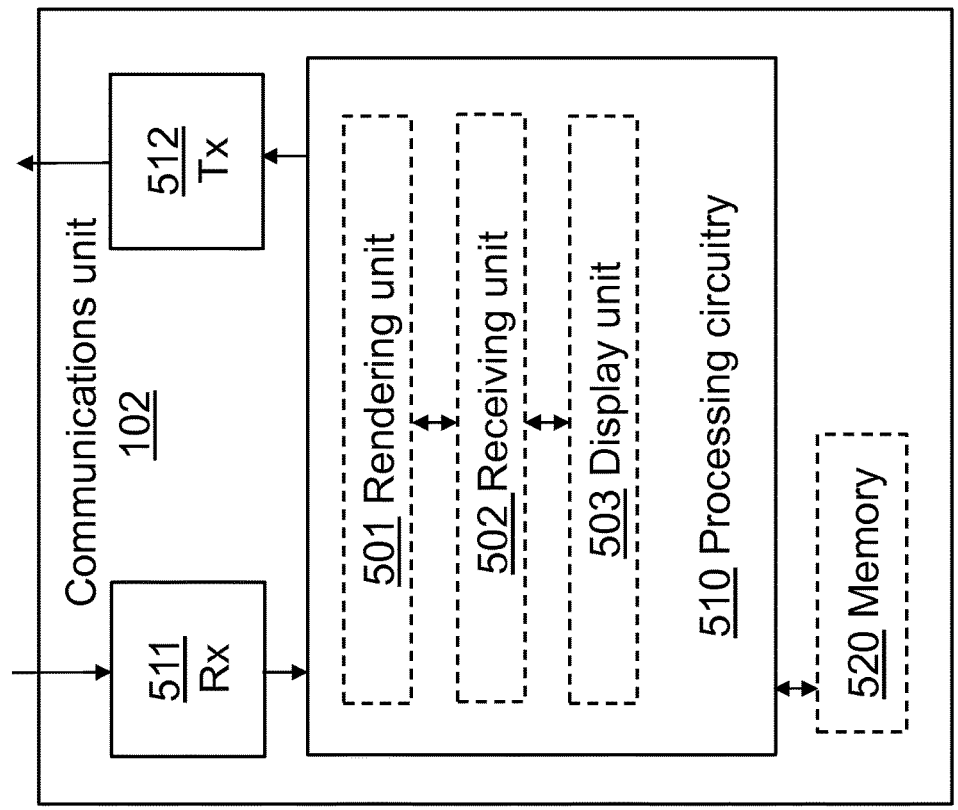
FIG. 5 is a block diagram depicting embodiments of a communication unit.

The communication unit 102 may comprise the following arrangement depicted in FIGS. 4 and 5.

FIG. 5 shows a schematic block diagram of embodiments of the first communications unit 102. The first network node is configured to be comprised in a communications network with at least one communication unit being located in each out of a number of vehicles.

The communication unit may comprise a rendering unit 501 which may also be referred to as a rendering device or circuitry. The rendering unit 501 is configured to render available a tire-to-road friction value (f) and a corresponding VSP (Vehicle State Parameter) (l, t) during the driving of the vehicle, each VSP comprising at least the geographical location (l) at which the tire-to-road friction value (f) is measured, and the instant in time (t) when the tire-to-road friction value (f) is measured.

The communication unit may comprise a receiving unit 502, which may also be referred to as a receiving device or circuitry. The receiving unit 502 is configured for receiving a result indicating a relative tire friction performance of the vehicle.

The communication unit may comprise a display unit 503, which may also be referred to as a display device or circuitry. The display unit 503 is configured for displaying said result to a driver of the vehicle.

The processing circuitry 410 may further comprise a receiver or receiving unit 411 and a transmitter or transmitting unit 412 for receiving/transmitting information to/from network nodes. The receiving and transmitting unit 411, 412 may alternatively be constituted by a transceiving unit.

The embodiments for rendering available a result to a driver of a vehicle through one or more processors, such as the processing circuitry 410 in the communications unit 102 depicted in FIG. 5, together with computer program code for performing the functions and actions of the embodiments herein. The program code mentioned above may also be provided as a computer program product, for instance in the form of a data carrier carrying computer program code or code means for performing the embodiments herein when being loaded into the processing circuitry 410 in the communication unit 102. The computer program code may e.g., be provided as pure program code in the communication unit 102 or on a server and downloaded to the communication unit 102.

The communication unit 102 may further comprise a memory 520 comprising one or more memory units. The memory 520 may be arranged to be used to store data, such as, e.g., the results received from the network node, to perform the methods herein when being executed in the communication unit 102.

Those skilled in the art will also appreciate that the processing circuitry 510 and the memory 520 described above may refer to a combination of analog and digital circuits, and/or one or more processors configured with software and/or firmware, e.g., stored in a memory, that when executed by the one or more processors such as the processing circuitry 510 perform as described above. One or more of these processors, as well as the other digital hardware, may be included in a single application-specific integrated circuit (ASIC), or several processors and various digital hardware may be distributed among several separate components, whether individually packaged or assembled into a system-on-a-chip (SoC).

Suitable hardware for communication units including display devices are known to a person skilled in the art.

A person skilled in the art, will readily understand that the communication unit, and method to be performed by a communication unit, may be modified in accordance with what is described in the above in relation to a network node and a method to be performed in a network node. For example, the VSP could include additional parameters to be rendered available by the communication unit, or the communication unit could be arranged to display various types of results.

The terminology used in the detailed description of the particular exemplary embodiments illustrated in the accompanying drawings is not intended to be limiting of the described network node and method, which instead are limited by the enclosed claims.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure.

What is claimed is:

1. A method performed by a network node for estimating a relative tire friction performance of a number of vehicles, wherein the network node and at least one communication unit located in each vehicle are comprised in a communications network, the method comprising:

receiving continuously tire-to-road friction values and corresponding Vehicle State Parameters (VSPs) from each communication unit in the number of vehicles during driving thereof, each VSP comprising at least a geographical location at which a tire-to-road friction value is measured and an instant in time when the tire-to-road friction value is measured;

determining that a tire-to-road friction value of a vehicle in the number of vehicles is comparative to at least one other tire-to-road friction value of another vehicle in the number of vehicles, when the corresponding VSP of said at least one other tire-to-road friction value deviates less than a predetermined deviation range from the corresponding VSP of the tire-to-road friction value of the vehicle;

comparing the tire-to-road friction value of the vehicle to the at least one other tire-to-road friction value of the another vehicle; and determining a ranking of a relative tire friction performance of the vehicle in relation to at least the another vehicle based on said comparison.

2. The method of claim 1 further comprising:
rendering information regarding the ranking available to the communication unit located in the vehicle.

3. The method of claim 1 further comprising:
retrieving said ranking;
performing a statistical evaluation of the ranking;
determining preselected relative tire friction performance levels based on said evaluation;
sorting the relative tire friction performance of the number of vehicles into groups based on the relative tire friction performance levels; and
rendering information about the group of the vehicle available to the communication unit located in the vehicle.

4. The method of claim 1 further comprising:
retrieving the number of comparative road friction values available in a data system;
determining whether said number is sufficient for performing a statistically valid analysis; and
generating a present validity status of the ranking based on said determination.

5. The method of claim 1 further comprising:
determining that the tire-to-road friction value of the vehicle deviates more than a predetermined variation range from a previous tire-to-road friction value of the vehicle;
determining that the variation is indicative of a change in conditions for that vehicle; and
deeming a VSP from the vehicle to be comparable to a VSP from another vehicle only if the instants in time and/or geographical locations of both VSPs are both before or after said change.

6. The method of claim 1 wherein the corresponding VSP of said at least one other tire-to-road friction value deviates less than a predetermined deviation range from the corresponding VSP of the tire-to-road friction value of a vehicle only if the difference between the location and/or instant of the corresponding VSP of the tire-to-road friction value of a vehicle and the location and/or instant of the corresponding VSP of the another tire-to-road friction value is less than a present predetermined location deviation L and/or a present predetermined time deviation T.

7. The method of claim 6 further comprising receiving information regarding the environmental conditions surrounding the vehicle and setting said location deviation L and/or time deviation T depending on the information regarding the environmental conditions surrounding the vehicle.

8. The method of claim 7 wherein said environmental conditions comprise at least one of weather conditions, ambient light conditions, and road conditions.

9. The method of claim 1 wherein each VSP further comprises a parameter including information regarding the vehicle configuration of the vehicle.

10. The method of claim 9 wherein the corresponding VSP of said at least one other tire-to-road friction value deviates less than a predetermined deviation range from the corresponding VSP of the tire-to-road friction value of a vehicle only if also said vehicle configurations are deemed comparable.

11. The method of claim 10 wherein the determination whether the vehicle configurations are comparable includes a comparison of at least one of vehicle weight and powertrain arrangement.

12. The method of claim 1 wherein the network node further comprises a map database including a geographical road condition status for the roads in the map database, the method further comprising:
weighing at least one tire-to-road friction value of a vehicle using said ranking so as to achieve at least one normalized road friction value; and
generating an updated geographical road condition status for the geographic map database using the at least one normalized road friction value.

13. The method of claim 12 further comprising rendering information about the geographical road condition status in the geographic map database available to the communication units of the vehicles.

14. A network node for estimating a relative tire friction performance of vehicles, wherein the network node and at least one communication unit for each of a number of vehicles (v) are comprised in a communications network, the network node comprising:
processing circuitry configured to receive continuously tire-to-road friction values and corresponding Vehicle State Parameters (VSPs) from each communication unit in the number of vehicles during driving thereof, each VSP comprising at least a geographical location at which a tire-to-road friction value is measured and an instant in time (t) when the tire-to-road friction value is measured;
wherein the processing circuitry is further configured to determine that a tire-to-road friction value of a vehicle in the number of vehicles is comparative to at least one other tire-to-road friction value of another vehicle in the number of vehicles, when the corresponding VSP of said at least one other tire-to-road friction value deviates less than a predetermined deviation range from the corresponding VSP of the tire-to-road friction value of the vehicle;
compare the tire-to-road friction value of the vehicle to the at least one other tire-to-road friction value of the another vehicle; and
determine a ranking of a relative tire friction performance of the vehicle in relation to at least the another vehicle based on said comparison.

15. A communication unit for communication with the network node of claim 14, the communication unit configured to be located in a vehicle, the communication unit comprising:
processing circuitry configured to continuously render available a tire-to-road friction value and a corresponding Vehicle State Parameter (VSP) during driving of a vehicle, each VSP comprising at least the geographical location at which the tire-to-road friction value is measured and the instant in time when the tire-to-road friction value is measured, the processing circuitry further configured to receive a result indicating a relative tire friction performance of the vehicle, and display said result to a driver of the vehicle.

* * * * *